United States Patent [19]

Ferrin et al.

[11] 4,107,270
[45] Aug. 15, 1978

[54] PROCESS FOR SIMULTANEOUS REMOVAL OF HYDROGEN SULFIDE AND WATER FROM A GAS MIXTURE WITHOUT SUBSTANTIAL REMOVAL OF CARBON DIOXIDE OR HYDROCARBONS

[75] Inventors: Charles Robert Ferrin; William Patrick Manning, both of Tulsa, Okla.

[73] Assignee: Combustion Engineering, Inc., Windsor, Conn.

[21] Appl. No.: 807,936

[22] Filed: Jun. 20, 1977

[51] Int. Cl.² .......................................... B01D 53/34
[52] U.S. Cl. ................................................. 423/226
[58] Field of Search .............. 423/226, 229, 228, 220; 55/68, 73

[56] References Cited

U.S. PATENT DOCUMENTS

| 1,783,901 | 12/1930 | Bottoms | 423/229 X |
| 3,965,875 | 6/1976 | Bratzler et al. | 423/220 |

FOREIGN PATENT DOCUMENTS

| 941,018 | 11/1963 | United Kingdom | 423/226 |

*Primary Examiner*—Earl C. Thomas
*Attorney, Agent, or Firm*—Arthur L. Wade

[57] ABSTRACT

A high boiling organic liquid, including 1-formylpiperidine or an alkylated derivative, is continuously applied to absorb hydrogen sulfide and water from a gas mixture, and is subsequently regenerated with heat.

4 Claims, 2 Drawing Figures

PROCESS FOR SIMULTANEOUS REMOVAL OF HYDROGEN SULFIDE AND WATER FROM A GAS MIXTURE WITHOUT SUBSTANTIAL REMOVAL OF CARBON DIOXIDE OR HYDROCARBONS

BACKGROUND OF THE INVENTION

1. Field of the Invention

This invention relates to a method for simultaneously sweetening and drying a gas stream.

More particularly, this invention relates to a process in which a high boiling, organic liquid is contacted under pressure with a natural gas stream to absorb the hydrogen sulfide and water without substantially altering the carbon dioxide or hydrocarbon content and is continuously regenerated.

2. Description of the Prior Art

The present practice is to condition produced, sour, natural gas for sale to a pipeline in two, separate processes. The first, and more severe, of the requirements is to reduce the sour, hydrogen sulfide, content to ¼ grain per 100 scf, or 4 ppm.

In a common method for sweetening gas, an aqueous solution of an amine and the sour gas are contacted counter-currently on a plurality of trays in a tower. Hydrogen sulfide forms a loose, addition compound with amines.

Thermal decomposition of the compound so formed occurs in a second trayed column equipped with a reboiler and condenser. The bottoms from the absorption column are fed to the regeneration column. The purified amine is withdrawn from the reboiler for continuous contact with the gas.

One of the problems with this process is that most amines also react with the carbon dioxide in the natural gas. Because the addition compound with carbon dioxide must also be decomposed, it is necessary to increase the circulation rate of the amine, the size of the regeneration column, and the reboiler heat load.

The second of the requirements for the produced natural gas is to reduce the water content to 5 pounds per MMscf, or 110 ppm. Dehydration is effected in a process very similar to that for sweetening. The main difference is the use of a glycol rather than an amine.

Glycol dehydration is practiced widely because of the moderate capital investment and the low operating cost. However, sweetening with an amine plant requires a considerable capital expenditure. There are many sour, natural gas wells for which the value of the produced gas is insufficient to justify the investment required for an amine system. For years, the iron sponge process has been the only economic way to sweeten such wells. While iron sponge does selectively remove hydrogen sulfide without absorbing carbon dioxide, the operation is so troublesome and the labor cost is so high, that many of these wells have not been produced.

Recently, a process has been developed using a slurry of zinc oxide in a zinc acetate solution to selectively absorb the hydrogen sulfide in the natural gas. The capital cost is relatively low, but the operating cost, though moderate, still limits the applicability to wells where the amount of hydrogen sulfide to be removed is not great.

While the zinc process certainly appears to be a very attractive alternative to the iron sponge process, both are best suited and, to an extent, limited to low pressure applications where a large contacting vessel can be constructed inexpensively.

A combination of monethanolamine and diethylene glycol has been used to dehydrate and sweeten natural gas. U.S. Pat. Nos. 2,177,068; 2,515,752 and 2,547,278 disclose such a process. In the disclosed system, the absorption tower is divided into two sections, so that the gas can be contacted successively with different aqueous solutions of the above liquids. These absorbents, or solvents, which first sweeten and then dry the gas, are regenerated separately in different reboilers. The flow pattern is fairly complicated, and obtaining good heat exchange between the streams makes the operation difficult to control. Also, after absorbing the hydrogen sulfide, the aqueous solution is quite corrosive. Furthermore, the capital investment required for this process is quite substantial.

N-methyl-2-pyrrolidone (M Pyrol) has been used as a sweetening solvent in the Purisol process. The Purisol process as disclosed in U.S. Pat. Nos. 3,324,627 and 3,120,933 uses three towers: absorber, reabsorber, and regenerator. The high pressure gas stream enters the bottom of the absorber and flows upward counter-currently to the lean M Pyrol which is introduced at the top of the absorber. After absorbing the hydrogen sulfide and water, the M Pyrol leaves the absorber and enters the intermediate pressure reabsorber. Some of the hydrogen sulfide and the dissolved hydrocarbons are flashed from the rich solvent in the bottom of the reabsorber and flow upward in counter-current contact with a portion of the regenerated solvent which enters the top tray of the reabsorber. The effluent gas from the reabsorber is used for plant fuel. The rich solvent together with the solvent fed to the top of the reabsorber, flows through a heat exchanger to the low pressure regeneration column. The hydrogen sulfide leaves at the top of the regeneration column, and the purified M Pyrol is pumped from the bottom of the regeneration column through the heat exchanger to the absorber and reabsorber columns.

There is a real need for a new sweetening process that will be suitable for high pressure, relatively low flow rate, gas streams provided that the capital outlay is reasonable and the operating cost is moderate. If the process can also dry the gas, the economic justification increases substantially — by both the investment and opeational cost of a glycol dehydrator.

An absorbent with a high selective affinity for hydrogen sulfide is required. Substantial rejection of carbon dioxide is necessary to prevent a prohibitively high flow rate when the sour gas stream to be treated also contains an appreciable amount of carbon dioxide.

A high affinity for water by the same absorbent is also required. But the presence of water must not significantly reduce the affinity of the absorbent for hydrogen sulfide.

Substantial rejection of hydrocarbons by the absorbent is required to limit the losses of the natural gas stream and the contamination of higher boiling hydrocarbons.

The absorbent must be thermally stable up to its boiling point. A high boiling point is required to reduce the absorbent losses and to facilitate the regeneration of the absorbent with heat.

Safety demands that the absorbent be non-toxic. It is highly desirable that the material not irritate the skin when it is handled.

Good heat transfer and fluid flow properties are very desirable for the absorbent. It should have a high thermal conductivity, a low specific heat and a low viscosity.

Finally, the absorbent must be non-corrosive to construction materials such as mild steel and aluminum.

SUMMARY OF THE INVENTION

It is an object of the invention to simultaneously remove hydrogen sulfide and water from a mixture of gases, which mixture may include carbon dioxide and hydrocarbons, without the substantial removal of the carbon dioxide or hydrocarbons.

The invention contemplates bringing a mixture of gases containing hydrogen sulfide and water which may include carbon dioxide and hydrocarbons into intimate contact with a liquid, high boiling, organic absorbent including 1-formylpiperidine, or an alkylated derivative thereof, and subsequently regenerating the absorbent for continuous contact with the mixture.

Other objects, advantages and features of the invention will become apparent to one skilled in the art upon consideration of the written specification, appended claims, and accompanying drawings.

DESCRIPTION OF THE PREFERRED EMBODIMENT

Figure 1:
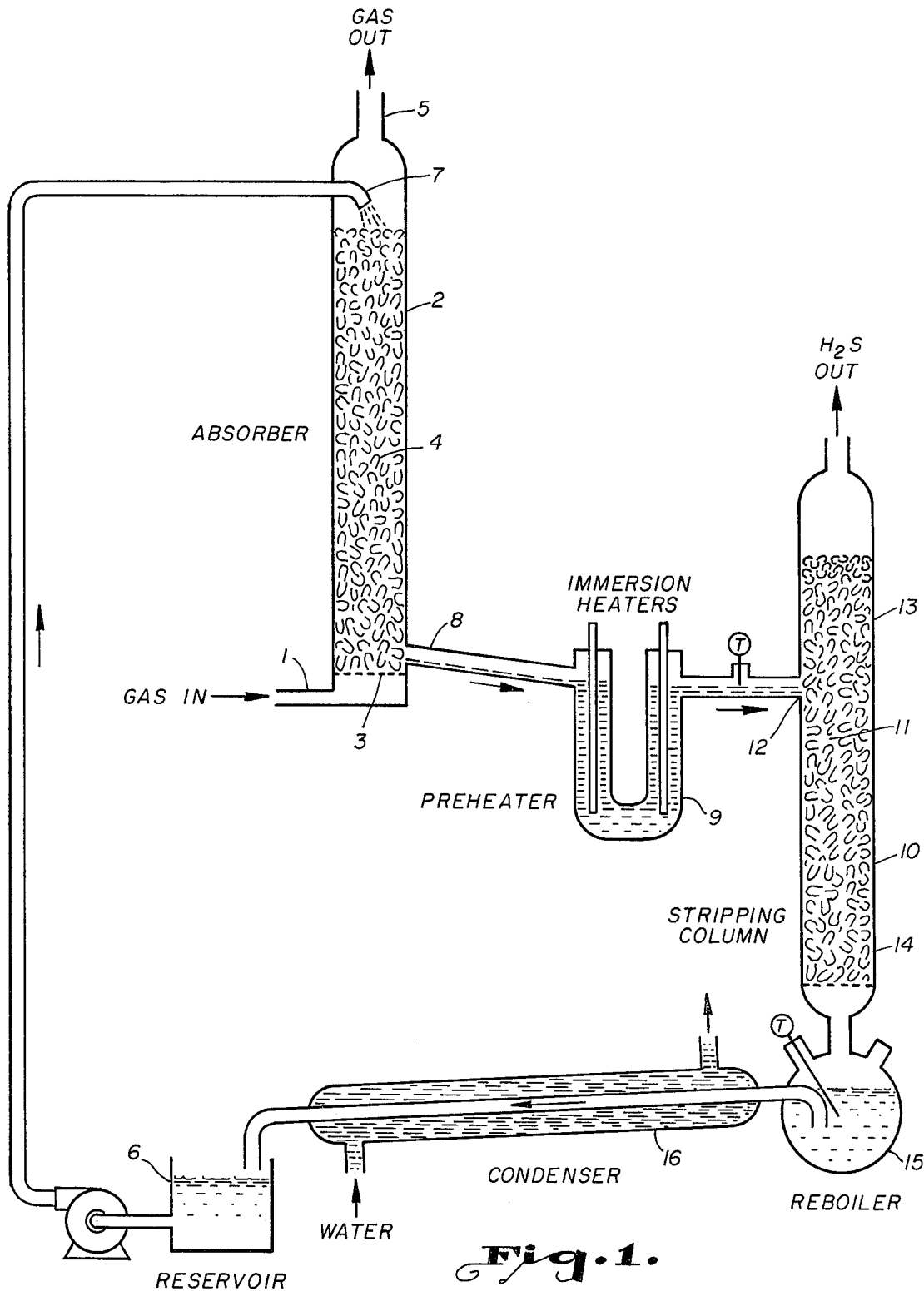
FIG. 1 is a diagrammatic elevation of pilot-scale apparatus in which the method embodying the invention is practiced.

To establish the feasibility of the process embodying the present invention, a pilot-scale unit was constructed to use absorbents which were successfully screened as to boiling point, viscosity and solubility of hydrogen sulfide, carbon dioxide and hydrocarbons. This pilot-scale unit was necessary to determine whether the screened absorbents will undergo cyclic hydrogen sulfide absorption and regeneration without degradation.

It was an objective that the pilot scale equipment resemble the commercial scale operation as closely as possible. Liquid-vapor contact columns with bubble-cap trays are impractical in the designed scale. So a 2 inch diameter by 30 inch long glass column packed with ½ inch Intalox saddles was prepared for the hydrogen sulfide absorption. A similar column, mounted on a 1-liter, three-necked flask, was assembled as the stripping column and regenerator.

The sour test gas flowed, through conduit 1, into the bottom of the absorption column 2 below sintered glass frit 3 which supports the packing 4. The conditioned gas left through the upper conduit 5. The cold, regenerated absorbent was pumped from the reservoir 6 to the side arm 7 just above the packing. After trickling over the packing, the absorbent left through the other side arm 8 just above the frit. The flow of test gas into the column up through the frit prevented any accumulation of the absorbent below the frit.

After preheating in the U-tube 9, the rich absorbent flowed into the regeneration column 10 at a position below the top of the packing 11. Above feed point 12, that portion of column 10 functioned as an air-cooled, reflux condenser 13. The lower portion of the column 10 was the stripping section 14. The heat required for solvent regeneration was supplied by a 380 watt heating mantle (not shown) around the flask 15, and a 200 watt heating tape (not shown) wrapped around the stripping section 14.

Because of the arrangement of the equipment, heat exchange between the hot and cold absorbent streams was impractical. So the feed to the stripping column was heated in the insulated U-tube preheater 9 equipped with two 470 watt immersion heaters. The hot bottoms from the reboiler 10 flowed through a vapor trap to a water-cooled condenser 16 which it was collected in the reservoir 6.

The test gas mixture, consisting of 0.5% hydrogen sulfide, 2.0% carbon dioxide and 97.5% natural gas, was obtained from a pressurized cylinder. The flow rate of the mixture was controlled by a regulator and a needle valve, monitored with a rotameter, and measured by the displacement of water from a graduated cylinder.

Thermometers were installed after the U-tube preheater and in the reboiler. Four powerstats controlled the heat supplied by the two immersion heaters in the U-tube, the heating mantle around the reboiler, and the heating tape around the stripping section.

Before conducting the gas mixture into the absorber, the absorbent circulation and operating temperatures were established. These are a flow rate of about 100 to 200 ml/min, vaporization of the absorbent in the reboiler, and an exit temperature from the U-tube that was 50° to 100° F below the boiling point. The ability to regenerate the absorbent limited the capacity of the system, and this regeneration was controlled by the total heat released by the immersion heaters and the heating mantle. When steady-state conditions were obtained, the gas mixture was fed to the absorber, and the flow rate increased until hydrogen sulfide was detected in the off-gas by the darkening of wet lead acetate paper.

The following tabulation is the operating data for 1-formylpiperidine and M Pyrol.

| Solvent | Liquid Flow Rate ml/min | Gas Flow Rate liter/min | Preheat Temp. ° F | Reboiler Temp. ° F |
| --- | --- | --- | --- | --- |
| 1-formyl piperidine | 100 | 1.0 | 330 | 435 |
| " | 120 | 1.5 | 374 | 431 |
| " | 180 | 2.0 | 338 | 437 |
| M Pyrol | 110 | 0.5 | 328 | 403 |
| " | 150 | 1.0 | 356 | 399 |

While both absorbents sweetened the gas mixture and were regenerated satisfactorily, the operation with 1-formylpiperidine is preferred because the ratio of liquid-to-gas flow rates is lower. Another advantage of 1-formylpiperidine is its higher boiling point. This characteristic reduces losses of the absorbent and facilitates thermal regeneration.

Figure 2:
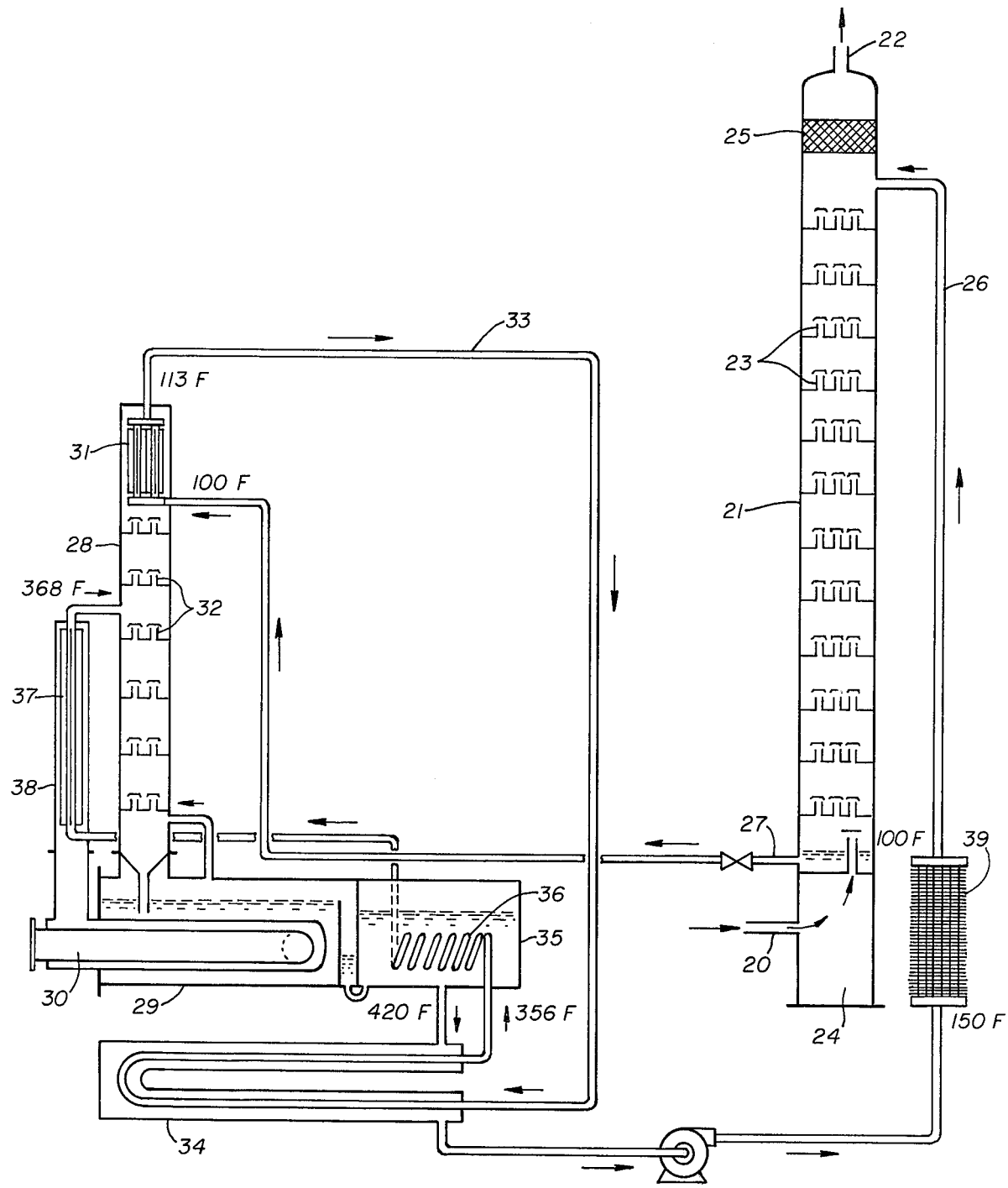
FIG. 2 is a diagrammatic elevation of a commercial form of the apparatus in which the method embodying the invention is practiced.

FIG. 2 discloses the preferred embodiment of the invention as carried out in a commercial form of apparatus. The disclosure contemplates that a stream of natural gas will be conditioned. More specifically, a 250 Mscfd stream at 250 psig containing 2000 ppm of hydrogen sulfide and 60 lbs. of water per MMscf was introduced by conduit 20 into absorber tower 21. The conditioned gas, containing 4 ppm of hydrogen sulfide and 5 lb per MMscf of water, was discharged from the top of tower 21 through conduit 22.

The absorption tower 21 has 12, bubble-cap trays 23 spaced vertically between a liquid-gas separator 24 at the bottom of the tower and a wire-mesh demister 25 at the top of the tower. The sour and wet gas stream entered separator 24, bubbled up through the liquid on each tray, and was discharged from the tower after passing through the demister.

The absorbent was conducted into tower 21 through conduit 26 and flowed downward from tray to tray. The absorbent left tower 21 through conduit 27, just above the separator 24. Twelve trays were found to be necessary for the process in its use of 1-formylpiperidine.

The material balance for the absorption of hydrogen sulfide is:

| Gas Mixture: | | | | |
|---|---|---|---|---|
| Flow rate | 250 Mscfd | or | 494 lb/hr | |
| Hydrogen sulfide in | 2,000 ppm | or | 0.0039 lb $H_2S$/lb gas | |
| Hydrogen sulfide out | 4 ppm | or | 7.6 $(10^{-6})$ lb $H_2S$/lb gas | |
| 1-formylpiperidine: | | | | |
| Flow rate | 10 gpm | or | 5,000 lb/hr | |
| Hydrogen sulfide in | | | 7.6 $(10^{-7})$ lb $H_2S$/lb absorbent | |
| Hydrogen sulfide out | | | 3.8 $(10^{-4})$lb $H_2S$/lb absorbent | |

At this point, it becomes evident to those skilled in the art that an alkylated derivative of 1-formylpiperidine will function satisfactorily in this process. Although there are more than one of the alkylated derivatives, an example serves to represent all of them.

To be definite, the formula for 1-formylpiperidine is set forth as $C_5 H_{10} N$ CHO. This material can also be represented by a diagram:

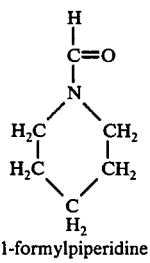

1-formylpiperidine

An alkylated derivative is 1-formyl, 2-methyl piperidine, set forth as $C_5 H_9 (CH_3)$ NCHO. This material can also be represented by a diagram:

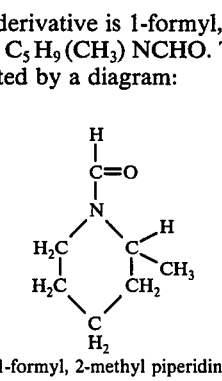

1-formyl, 2-methyl piperidine

The absorbent in conduit 27 was regenerated in column 28 which was mounted on the cylindrical reboiler 29 with a firetube 30. Condenser 31 was positioned in the top of column 28 to reduce the 1-formylpiperidine losses and to supply the reflux needed for good separation of hydrogen sulfide and 1-formylpiperidine.

Specifically, column 28 had six bubble-cap trays 32. While a packed bed could have been used, trays are preferred because, for a given height, a larger number of theoretical stages can be obtained with trays than with a packed bed.

When the rich absorbent was conducted through condenser 31, it was heated from 100° to 113° F. In conduit 33, the absorbent was heated by regenerated, hot absorbent, in the double-pipe heat exchanger 34. The temperature of the absorbent was increased to 356° F. Further preheating of the absorbent was carried out in the surge tank 35, coil 36 and a single-pass coil 37 mounted through the stack 38 of reboiler 29. The final, preheat temperature of the absorbent was 368° F.

The number of theoretical trays needed to regenerate the 1-formylpiperidine can be decreased by either increasing the reflux ratio or decreasing the heat content of the absorbent feed. But both of these increase the reboiler duty and, therefore, the operating cost. A reflux ratio as high as 40 to 1 is practical because the amount of distillate produced is very small — about 1.05% of the feed. This enables the feed to be preheated to the limit obtainable in the heat exchanger without unduly increasing the number of theoretical trays.

The material balance for the regeneration is:

| Feed: | | | | |
|---|---|---|---|---|
| Hydrogen sulfide | 1.9 | lb/hr | or | 3.8 $(10^{-4})$lb $H_2S$/lb absorbent |
| 1-formylpiperidine | 5000.0 | | | |
| | 5001.9 | | | |
| Distillate: | | | | |
| Hydrogen sulfide | 1.9 | lb/hr | or | 0.79 lb $H_2S$/lb absorbent |
| 1-formylpiperidine | 0.5 | | | |
| | 2.5 | | | |
| Bottoms: | | | | |
| Hydrogen sulfide | 0.0 | lb/hr | or | 7.6 $(10^{-7})$lb $H_2S$/lb absorbent |
| 1-formylpiperidine | 4999.5 | | | |
| | 4999.5 | | | |

Good heat exchange between the hot, lean 1-formylpiperidine from the reboiler and the cold, rich 1-formylpiperidine from the absorber is the prime requirement for efficient operation. It is accomplished by the coil in the surge tank of the reboiler and the double-pipe heat exchanger connected between the reboiler and the absorber. The arrangement—parallel and/or series—depends on the 1-formylpiperidine flow rate. The hot 1-formylpiperidine flows shell-side where the pressure drop is small enough to be overcome by the suction of the pump. In this way, the pump is located where the 1-formylpiperidine is relatively cool.

Additional cooling of the lean 1-formylpiperidine for the absorber can be obtained by an air-cooled heat exchanger 39 between the pump and the 1-formylpiperidine inlet to the absorber. Also, the exit 1-formylpiperidine stream from the absorber is used as the coolant for the condenser 31 in the regeneration column.

The firing rate in the reboiler must be controlled by the vapor flow rate to the stripping column. This is accomplished by a liquid seal on the 1-formylpiperidine entering the reboiler from the column and a separate conduit for returning the vapor. The differential pressure across an orifice in the vapor line is the control signal for the fuel gas valve.

Mandatory safety devices are included to control the 1-formylpiperidine level in the surge tank of the reboiler and an excessive gas temperature leaving the condenser.

From the foregoing, it will be seen that this invention is one well adapted to attain all of the ends and objects hereinabove set forth, together with other advantages which are obvious and inherent to the process.

It will be understood that certain features and subcombinations are of utility and may be employed without reference to other features and subcombinations. This is contemplated by and is within the scope of the invention.

As many possible embodiments may be made of the invention without departing from the scope thereof, it is to be understood that all matter herein set forth or shown in the accompanying drawings is to be interpreted in an illustrative and not in a limiting sense.

The invention having been described, what is claimed is:

1. The process for the separation of hydrogen sulfide and water from a mixture of natural gases which may also contain carbon dioxide, which comprises, scrubbing the mixture of gases with a liquid, high boiling organic absorbent selected from the group consisting of 1-formyl piperidine and alkylated derivatives of 1-formyl piperidine in an absorption zone above atmospheric pressure to thereby absorb both the hydrogen sulfide and water but substantially less of the carbon dioxide and hydrocarbons, conducting the absorbent containing the hydrogen sulfide and water to a desorption zone at atmospheric pressure liberating the absorbed hydrogen sulfide and water from the absorbent to thereby regenerate the absorbent, and recycling the regenerated absorbent to the absorption zone.

2. The process of claim 1 in which the absorbent includes an alkylated derivative of 1-formylpiperidine.

3. The process of claim 1 wherein the hydrogen sulfide and water are liberated at atmospheric pressure by heating the absorbent.

4. The process of claim 3 wherein the regenerated absorbent is heat-exchanged with the absorbent after it was scrubbed the mixture of natural gases.

* * * * *